United States Patent [19]

Lee et al.

[11] Patent Number: 5,637,345
[45] Date of Patent: *Jun. 10, 1997

[54] METHOD OF MANUFACTURING POWDERED DEER BLOOD

[75] Inventors: Youn S. Lee, Christchurch, New Zealand; Hyung S. Lee, Seoul, Rep. of Korea

[73] Assignee: National Deer Horn Limited, Christchurch, New Zealand

[*] Notice: The term of this patent shall not extend beyond the expiration date of Pat. No. 5,460,677.

[21] Appl. No.: 584,748

[22] Filed: Jan. 11, 1996

Related U.S. Application Data

[63] Continuation-in-part of Ser. No. 284,159, Aug. 2, 1994, Pat. No. 5,505,980.

[30] Foreign Application Priority Data

Aug. 2, 1993 [NZ] New Zealand ............................ 248309

[51] Int. Cl.$^6$ ............................ A23L 1/311; A23L 1/313
[52] U.S. Cl. ............................ 426/647; 426/385; 426/444; 426/473
[58] Field of Search ............................ 426/647, 385, 426/444, 473

[56] References Cited

U.S. PATENT DOCUMENTS

| | | | |
|---|---|---|---|
| 4,098,780 | 7/1978 | Lindroos | 426/647 X |
| 4,330,463 | 5/1982 | Luijerink | 426/647 X |
| 4,446,066 | 5/1984 | Luijerink | 426/647 X |
| 4,666,725 | 5/1987 | Yamashita et al. | 426/647 X |
| 4,986,998 | 1/1991 | Yoo et al. | 426/647 |

FOREIGN PATENT DOCUMENTS

| | | | |
|---|---|---|---|
| 1-211452 | 8/1989 | Japan | 426/647 |
| 1738219 | 6/1992 | U.S.S.R. | 426/647 |

*Primary Examiner*—Arthur L. Corbin
*Attorney, Agent, or Firm*—Merchant, Gould, Smith, Edell, Welter & Schmidt

[57] ABSTRACT

Powdered deer blood, preferably that of a stag, can be produced according to a method which comprises the steps of freezing the blood of a deer, cutting the frozen blood into slices, freeze-drying the slices of frozen blood and grinding down the freeze-dried blood into a powder. The invention also relates to the product formed from the aforementioned method.

8 Claims, No Drawings

METHOD OF MANUFACTURING POWDERED DEER BLOOD

This application is a continuation-in-part of Ser. No. 284,159, filed Aug. 2, 1994, now U.S. Pat. No. 5,505,980.

FIELD OF THE INVENTION

The present invention relates to a health food including as its main component powdered deer blood and a manufacturing method for making the health food.

BACKGROUND OF THE INVENTION

In Korea and China deer blood, particularly that of a stag, has been served since ancient times as a high quality food which promotes energy and health.

The stag deer blood has been used in foodstuff for promoting physical strength or as food for a patient. Moreover as a food it contains various nutritious components. In particular deer blood has been used as a miraculous medicine with Ginseng and Velvet.

In a traditional Korean medical book (Dong Eui Bo Gam, Eastern Medical Dictionary), it is mentioned that deer blood has an effect on the feeble, palpation, insomnia, uterine, haemorrhage, impotence etc.

Until now, no one has produced deer blood other than from velvet produced on a farm.

In spite of being a useful food, there are problems with respect to quality. For example, decaying or changing of colour is prevalent. Therefore, even though pure powdered stag deer blood has been known for a long time to have these uses, no high quality product of this type is currently available.

SUMMARY OF THE INVENTION

The object of the present invention is to provide an enriched nutritious food including mainly a powder made from deer blood, which is kept fresh and sterilized, and also a manufacturing method therefor. Preferably the deer blood is from a stag.

Another object of the present invention is to provide a food which can be taken by itself or by adding it to or mixing it with other foods or which can be used as raw material for processed foods.

According to the first aspect of the present invention there is provided a method of manufacturing powdered deer blood, comprising the steps of:

freezing the blood of a deer;

cutting the frozen blood into slices;

freeze-drying the slices of frozen blood; and grinding down the blood into powder.

The method for producing powdered deer blood can comprise the steps of:

collecting blood in a hygienic manner from a healthy deer;

keeping the blood frozen in a refrigerator at −20° C. to −40° C.;

cutting the frozen deer blood into slices about 15 mm in thickness;

laying the slices on a tray;

loading the tray into a freeze-dry machine;

freeze-drying the blood over a 24 hour drying cycle to a moisture content of less than 5%;

applying a vacuum to the drying chamber of the freeze-drying machine; and applying heat slowly to the product so that the product stays frozen and is dried at less than 0° C.

Towards the end of the drying cycle, the temperature can be raised to finish drying at 40° C. After that it can be cooled to 20° C. and loaded into drums awaiting quality control clearance.

The dried blood can be ground down to a fine powder having a grade 200 mesh.

In the case of the freeze-dried product, it has a limited storage life. However the product produced by double drying while it is heated between 35° C. to 40° C. after the freeze-drying makes the powder more stable for storage.

The powdered deer blood product is convenient to deal with and is easily blended with not only water but various other raw materials.

Also, the powder is very useful as a raw material for processed foods and it has a high nutritional value.

The powder contains many quality proteins, amino acids, minerals, vitamins and therefore the powder can be used as a health food.

A general analysis of the powder is shown in the following Table 1.

TABLE 1

| DESCRIPTION | COMPONENT | VALUE | UNIT |
| --- | --- | --- | --- |
| MOISTURE | MOISTURE | 2.98 | g/100 g |
| ORGANIC MATERIALS | Ash | 5.6 | g/100 g |
| | Fat | 0.13 | g/100 g |
| | Protein | 93.2 | g/100 g |
| MINERAL | Se | 5.66 | ug/100 g |
| | Ca | 7.65 | mg/100 g |
| | NaCl (Salt) | 7.0 | mg/100 g |
| | P | 8.0 | mg/100 g |
| | Mg | 3.26 | mg/100 g |
| | Fe | 0.28 | g/100 g |
| | Zn | 1.39 | mg/100 g |
| | Cu | 0.06 | mg/100 g |
| HORMONE | Thyroxin | On Study | |
| | Posterior Pituitary | On Study | |
| | Androgen | On Study | |
| | Testesterone | On Study | |
| VITAMIN | Vitamin A | 434.2 | I.U/100 g |
| | Vitamin B1 | 0.2 | mg/100 g |
| | Vitamin B2 | 0.7 | mg/100 g |
| | Vitamin E | 1.8 | mg/100 g |
| | Niacine | 4.9 | mg/100 g |

In the complete analysis of the powder the level of raw bacteria is generally below 500/g and there is no detection of tar pigment or salmonella.

The powder contains the amino acids shown in Table 2 below and vitamins such as A, B1, B2, E and Niacine. It can be called an "albuminuous food" because it contains 94 g protein per 100 g powder.

TABLE 2

| ITEMS | VALUE (per 100 g) | ITEMS | VALUE (per 100 g) |
| --- | --- | --- | --- |
| Lysine | 6.4 g | Serine | 3.8 g |
| Histidine | 5.4 g | Glutamic Acid | 6.92 g |
| Arginine | 3.7 g | Proline | 3.12 g |
| Aspartic Acid | 8.45 g | Glycin | 3.41 g |
| Teroin | 8.26 g | Alanine | 7.7 g |

DESCRIPTION OF THE PREFERRED EMBODIMENTS

The following description relates to the preferred embodiments of the powder. The preferred embodiments are described for reference only and are not intended to be limiting.

The first embodiment is an enriched nutritious food including pure powdered stag's deer blood produced according to the aforegoing manufacturing method.

The enriched food can be utilised in nutrition and as an additional raw material for healthy food and Chinese medicines.

The second embodiment is in the form of an enriched nutritious capsule made by the following procedure.

Firstly, the powder in an amount of 2% to 30% is mixed with 2% to 90% squalene. Next, this mixture is added to vitamin E, recitin and other auxiliary materials in the proportion of 8% to 68%. After that, the mixture is encapsulated in gelatine capsules.

The percentages given above are percentages by weight.

The reason for adding squalene, which can be extracted from shark liver oil, is to promote the production of energy and oxygen in the body and the oxygen transfer of proteins (the main component of deer blood), to the whole body, and acts like Vitamin A, D, E.

As a result of this high metabolism, the blood is ventilated and increases the body's immunity. Moreover, it is considered to be effective in age-resistance, cytogenesis and the endocrine system.

The mixture of deer blood powder and squalene is a good health food which activates bodily functions effectively.

In addition to the above auxiliary materials, the present invention can contain extracts of vegetables such as ginseng, licorice, ganoderma and vitamins such as A, B, C, D, and E, pyridixine, hydrochlorides, cyanocobalmin, nicotinamide, sodium bicarbonate, glutamate and such amino acids as glycine, alanine, iso-leucine, L-phenylalanine, L-lysine and tryptophan.

Also it can contain royal jelly and/or honey. Corn oil, bean oil, cotton-seed oil, sesame oil, wheatgerm oil, palm oil, recitin, glyceride oil improve the convenience of encapsulating.

The third embodiment is in the form of enriched nutritious granules made by the following procedure. First, the following ingredients are mixed:

Stag deer blood powder (60% to 80%); Ginseng powder (10% to 20%), pollen (2% to 5%); and honey (5% to 15%) as an excipient.

After that, the mixture of the powder is wrapped with parafin wax in order to improve the storage life of the product.

What is claimed is:

1. A method of manufacturing powdered deer blood comprising the steps of:

freezing blood of a deer;

cutting the frozen blood into slices;

freeze-drying the slices of frozen blood;

grinding the freeze-dried blood into a powder.

2. A method as claimed in claim 1 wherein the blood is frozen at about $-20°$ C. to $-40°$ C.

3. A method as claimed in claim 2 wherein the slices are substantially 20 mm to 50 mm thick.

4. A method as claimed in claim 2 wherein the slices are freeze-dried over a 24 hour drying cycle at about $35°$ C. to $40°$ C. so that the slices have a moisture content of less than about 5%.

5. A method as claimed in claim 2 wherein the powder has a grade of about 200 mesh or smaller.

6. A method as claimed in claim 1 wherein the slices are substantially 20 mm to 50 mm thick.

7. A method as claimed in claim 1 wherein the slices are freeze-dried over a 24 hour drying cycle at about $35°$ C. to $40°$ C. so that the slices have a moisture content of less than about 5%.

8. A method as claimed in claim 1 wherein the powder has a grade of about 200 mesh or smaller.

* * * * *